United States Patent [19]
Takalo et al.

[11] Patent Number: 6,080,839
[45] Date of Patent: Jun. 27, 2000

[54] LABELING REACTANTS AND THEIR USE

[75] Inventors: Harri Takalo; Jari Hovinen, both of Turku; Veli-Matti Mukkala, Kaarina; Päivi Liitti; Heikki Mikola, both of Turku, all of Finland

[73] Assignee: Wallac Oy, Turku, Finland

[21] Appl. No.: 09/104,219

[22] Filed: Jun. 25, 1998

[51] Int. Cl.$^7$ .......................... C07K 1/13; G01N 33/533; C07D 221/00

[52] U.S. Cl. .............................. 530/334; 435/6; 436/546; 546/82; 546/140; 546/147; 546/256; 546/257; 546/270.4; 546/272.4; 546/275.4; 546/280.4; 546/329; 546/335; 546/336; 546/339; 546/340; 548/545; 560/27; 560/29

[58] Field of Search ............................... 546/81, 139, 256, 546/257, 279.4, 82, 140, 147, 270.4, 272.4, 275.4, 280.4, 329, 335, 336, 339, 340; 436/544, 817, 546; 530/334; 435/6; 548/545; 560/27, 29

[56] References Cited

U.S. PATENT DOCUMENTS

| | | | |
|---|---|---|---|
| 4,837,169 | 6/1989 | Toner ........................................ | 436/546 |
| 5,324,825 | 6/1994 | Kankare et al. ........................... | 534/16 |
| 5,571,897 | 11/1996 | Takalo et al. .............................. | 534/15 |
| 5,859,215 | 1/1999 | Rodriguez-Ubis et al. ............... | 534/16 |

OTHER PUBLICATIONS

Erlanger, Methods in Enzymology, vol. 70, Immunochemical Techniques, Part A, 85–104 (1980).
Brinkley, Bioconjugate Chemistry, vol. 3, 2–13 (1992).
Wong, Chemistry of Protein Conjugation and Cross–Linking, Chapter 2 (1991).

*Primary Examiner*—Mary E. Ceperley
*Attorney, Agent, or Firm*—Lydon & Brown, LLP

[57] ABSTRACT

The invention relates to a novel labeling reactant, suitable for labeling of a biospecific binding reactant using solid-phase synthesis. The invention further concerns new labeling methods. The novel labeling reactant has the formula (I)

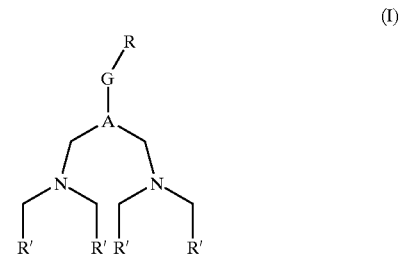

(I)

wherein

-A- is a bivalent aromatic structure capable of absorbing light or energy and transferring the excitation energy to a lanthanide ion after the product made by the said solid-phase synthesis has been released from the used solid support, deprotected and converted to a lanthanide chelate;

-G- is a bridge replacing a hydrogen atom in A;

R is a protected amino acid residue —CH(NHX)COOH, where X is a transient protecting group, or its active ester, where said ester is e.g. an N-hydroxysuccinimido, p-nitrophenol or pentafluorophenol ester; and R' is —COOR''' where R''' is an alkyl of 1 to 4 carbon atoms, phenyl or benzyl, which phenyl or benzyl can be substituted or unsubstituted.

22 Claims, 2 Drawing Sheets

LABELING REACTANTS AND THEIR USE

FIELD OF THE INVENTION

This invention relates to novel compounds suitable for labeling of a biospecific binding reactant using solid-phase synthesis. The invention relates further to novel methods of labeling a biospecific binding reactant in a solid-phase synthesis.

BACKGROUND OF THE INVENTION

The publications and other materials used herein to illuminate the background of the invention, and in particular, cases to provide additional details respecting the practice, are incorporated by reference.

Solid-phase synthesis is a well-known and widely spread technology in modern organic chemistry for preparation of various biologically important compounds. It has found many new applications such as combinatorial libraries and the peptide-based DNA analogue (PNA, peptide nucleic acids). Along with the technology development, the need for labeling those biologically interesting compounds during solid-phase synthesis has appeared. Several non-fluorescent labeling candidates have been published (Arya, R. and Gariépy, J., 1991, Bioconjugate Chem., 2, 323, Cuenoud, B. and Schepartz, A., 1991, Tetrahedron, 47, 2535, Rana, T. M., Ban, M. and Hearst, J. E., 1992, Tetrahedron Lett., 33, 4521, Song, A. I. and Rana, T. A., 1997, Bioconjugate Chem., 8, 249). These labels have been developed mainly to incorporate metal ions such as Fe, Cu in a peptide to act as sequence-specific cleaving agents for proteins. Radioactive $^{153}$Gd, $^{111}$In etc. can be used for in vivo tumor localization and radioimmunotherapy. Using lanthanide ions and a separate luminescence enhancement step these published monomers can be used as luminescent labels but a separate enhancement step is needed to produce the luminescence to be detected. During the luminescence enhancement the lanthanide has to be dissociated from the label and then spatial information will be lost.

Fluorescent label monomers for solid-phase synthesis have been published (Lohse, J., Nielsen, P. E., Harrit, N. and Dahl, O., 1997, Bioconjugate Chem., 8, 503, McCafferty, D. G., Bishop, B. M., Wall, C. G., Hughes, S. G., Mecklenberg, S. L., Meyer, T. J. and Erickson, B. W., 1995, Tetrahedron, 51, 1093, WO 96/03409). Fluorescein and other organic chromophores were used in those studies. However, such labels and labeled biomolecules suffer from many commonly known drawbacks such as Raman scattering, other fluorescent impurities, low water solubility, concentration quenching etc.

In the specific binding assays, such as e.g. immunoassays, DNA hybridization assays, receptor-binding assays, and cellular binding assays, generally very low concentrations of the analytes to be measured are present. Therefore, various labeling compounds have been developed that allow the labeled reactant to be detected and quantitated with high sensitivity. In immunoassays and DNA hybridization assays, time-resolved luminescence spectroscopy using lanthanide chelates is well known. (e.g. I. Hemmilä, T. Ståhlberg, and P. Mottram (eds.), "Bioanalytical Applications of Labeling Technologies", Wallac, Turku, 1994). Stable photoluminescent (in this context simply referred to as luminescent) lanthanide chelates also have other applications, e.g. fluorescence microscopy and cytometry. Therefore, a number of attempts have been made to develop new highly luminescent chelate labels suitable for those types of time-resolved fluorometric applications. These include e.g. stable chelates composed of derivatives of pyridines (U.S. Pat. No. 4,920,195, U.S. Pat. No. 4,801,722, U.S. Pat. No. 4,761,481, PCT WO FI-91/00373, U.S. pat. appl. Ser. No. 08/135,525, EP Appl. 0770610, Remuiñan, M. J., Román, H., Alonso, M. T. and Rodríguez-Ubis, J. C., 1993, J. Chem. Soc., Perkin Trans.2, 1099), bipyridines (U.S. Pat. No. 5,216,134), terpyridines (U.S. Pat. No. 4,859,777, U.S. Pat. No. 5,202,423, U.S. Pat. No. 5,324,825) or various phenolic compounds (U.S. Pat. No. 4,670,572, U.S. Pat. No. 4,794,191, Ital. Pat. 42508 A/89) as the energy mediating groups and polycarboxylic acids as chelating parts. In addition, various dicarboxylate derivatives (U.S. Pat. No. 5,032,677, U.S. Pat. No. 5,055,578, U.S. Pat. No. 4,772,563), macrocyclic cryptates (U.S. Pat. No. 4,927,923, PCT WO 93/5049, EP-A493,745) and macrocyclic Schiff bases (EP-A369,000) have been patented. None of these patents and articles present any methods for labeling of a biospecific binding reactant such as a hapten, a peptide, a receptor ligand, a drug or PNA oligomer, with luminescent labels by using solid-phase synthesis.

OBJECTS AND SUMMARY OF THE INVENTION

A main purpose of the present invention is to solve the problems associated with labeling of small molecules with luminescent chelates and to develop easier labeling methods. By preparing suitable ligand structures together with solid-phase synthesis the labeling of small molecules with directly luminescent lanthanide chelates is achievable.

One object of this invention is to provide a novel labeling reactant suitable for labeling of a biospecific binding reactant using solid-phase synthesis.

Another object of the present invention is to provide a novel method for labeling of a biospecific binding reactant in solid-phase synthesis.

Yet another object of the present invention is to provide the method of labeling a biospecific binding reactant with an exact, predetermined number of labeling reactants (one or several).

Thus according to one aspect, the present invention concerns a novel labeling reactant of formula (I) suitable for labeling of a biospecific binding reactant using solid-phase synthesis (I)

wherein

-A- is a bivalent aromatic structure capable of absorbing light or energy and transferring the excitation energy to a lanthanide ion after the product made by the said solid-phase synthesis has been released from the used solid support, deprotected and converted to a lanthanide chelate;

-G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR"- and —NR"—CO—), ester (—COO— and —OOC—), disulfide (—S—S—), diaza (—N=N—) and tertiary amine (—NR"-), wherein R" represents an alkyl containing less than 5 carbon atoms;

R is a protected amino acid residue —CH(NHX)COOH, where X is a transient protecting group, or its active ester, where said ester is e.g. an N-hydroxysuccinimido, p-nitrophenol or pentafluorophenol ester; and R' is —COOR'" where R'" is an alkyl of 1 to 4 carbon atoms, phenyl or benzyl, which phenyl or benzyl can be substituted or unsubstituted.

According to another aspect, this invention concerns a novel method of labeling a biospecific binding reactant in a solid-phase synthesis. Said method comprises the steps of a) reacting a labeling reactant of formula (I)

(I)

wherein

-A- is a bivalent aromatic structure capable of absorbing light or energy and transferring the excitation energy to a lanthanide ton after the product made by the said solid-phase synthesis has been released from the used solid support, deprotected and converted to a lanthanide chelate;

-G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR"- and —NR"—CO—), ester (—COO— and —OOC—), disulfide (—S—S—), diaza (—N=N—) and tertiary amine (—NR"-), wherein R" represents an alkyl containing less than 5 carbon atoms;

R is a 4-substituted 6-chloro-1,3,5-triazine-2-amine, isothiocyanato, bromoacetamido, iodoacetamido, pyridyldithio, amino, thiol, carboxylic acid residue or its active ester, a protected amino acid residue —CH(NHX)COOH, where X is a transient protecting group, or its active ester, where said ester is e.g. an N-hydroxysuccinimido, p-nitrophenol or pentafluorophenol ester; and R' is —COOR'" where R'" is an alkyl of 1 to 4 carbon atoms, phenyl or benzyl, which phenyl or benzyl can be substituted or unsubstituted, with a functional group which is bound to a solid phase, b) cleaving the product obtained in step a) from the solid phase, converting R' to —COOH, and removing optional protection groups, c) converting the product from step b) to a lanthanide chelate, and d) in case the functional group mentioned in step a) is not part of the final biospecific binding specific reactant, attaching said biospecific binding reactant to the lanthanide chelate obtained in step c).

According to yet another aspect, this invention concerns a novel method of labeling a biospecific binding reactant with an exact, predetermined number of labeling reactants of formula (I) in a solid-phase synthesis, said method comprising the steps of a) reacting a labeling reactant of formula (I)

(I)

wherein

-A- is a bivalent aromatic structure capable of absorbing light or energy and transferring the excitation energy to a lanthanide ion after the product made by the said solid-phase synthesis has been released from the used solid support, deprotected and converted to a lanthanide chelate;

-G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR"- and —NR"—CO—), ester (—COO— and —OOC—), disulfide (—S—S—), diaza (—N=N—) and tertiary amine (—NR"-), wherein R" represents an alkyl containing less than 5 carbon atoms;

R is a protected amino acid residue —CH(NHX)COOH, where X is a transient protecting group, or its active ester, where said ester is e.g. an N-hydroxysuccinimido, p-nitrophenol or pentafluorophenol ester; and R' is —COOR'" where R'" is an alkyl of 1 to 4 carbon atoms, phenyl or benzyl, which phenyl or benzyl can be substituted or unsubstituted, with a functional group which is bound to a solid phase, b) removing the transient protecting group X and optionally other transient protecting groups attached to the solid phase, c) reacting the labeling reactant of formula (I) with a deprotected functional group attached to the solid phase, d) optionally repeating the steps b) to c) the number of times necessary to achieve the exact, predetermined number of labeling reactants of formula (I) bound to the solid phase, e) cleaving the product obtained after the final step c) from the solid phase, converting R' to —COOH, removing the group or groups that have bound the product to the solid phase, and removing optional protecting groups, and f) converting the product from step e) to a lanthanide chelate.

DETAILED DESCRIPTION OF THE INVENTION

The novel labeling reactants and novel labeling methods according to the present invention are particularly suitable in the labeling of small molecules. Said small molecules are biospecific binding reactants including but not limited to antigens, haptens, peptides, receptor ligands, drugs or PNA oligomers which are used in specific bioaffinity based binding assays, such as immunoassays, DNA hybridization assays, receptor binding assays, immunocytochemical or immunohistochemical assays utilizing fluorometric or time-resolved fluorometric determination of the specific luminescence.

Particularly preferable transient protecting groups X are fluorenylmethyloxycarbonyl (Fmoc) or tert-butyloxycarbonyl (Boc).

The substituent R'" is preferably methyl, ethyl or tert-butyl.

The term "bivalent" in the definition of -A- shall mean a chemical group bound to two neighboring atoms.

The bivalent aromatic structure -A- is preferably selected from a group consisting of the structures disclosed in Scheme 1.

Most preferably, the labeling reactant is either 6-{N-{4-{2"-{2'",6'"-bis{N,N-bis[(tert-butoxycarbonyl)methyl]aminomethyl}-4'"-pyridyl}ethynyl}phenoxymethylcarbonyl}amino]-2-[-N-(fluorenylmethyloxycarbonyl)amino]hexanoic acid (5), or 6-{N-{4'-{2"-{1'",3'"-bis[(tert-butoxycarbonyl)-methyl]aminometh-5""-yl-2""-pyridyl}-1H-pyrazol-4'"-yl}ethyl}phenoxymethylcarbonyl}amino-2-[N-(fluorenylmethyloxycarbonyl)amino]hexanoic acid (10).

According to a preferred embodiment of the invention the lanthanide chelate is a europium(III), terbium(III), samarium(III) or dysprosium(III) chelate.

The labeling of said biospecific binding reactants is performed by using solid-phase synthesis methods. It has appeared desirable to prepare suitable protected monomers that could be incorporated into said biospecific binding reactants during solid-phase synthesis. The labeling reactants of the present invention form a luminescent labeled biospecific binding reactant after releasing the product from solid support, deprotection and addition of a suitable lanthanide ion. The labeling technique of the present invention has many advantages over conventional labeling in liquid phase, such as high yields of easily purified products, straightforward routine automation leads to improved robustness, upscaling and repeatability of synthesis and labeling of biospecific binding reactant with an exact number of stable luminescent lanthanide chelates is possible. Although many of the advantages relate to solid-phase labeling, the compounds of the present invention can also be used in liquid phase labeling.

The labeling reactants and the methods of this invention combine several important features, such as:

aromatic structure capable of absorbing light or energy and transferring the excitation energy to a lanthanide ion after the product made by the said solid-phase synthesis has been released from the used solid support, deprotected and converted to a lanthanide chelate, functional group or groups allowing efficient coupling of the compound to the said biospecific binding reactant without destroying its binding properties and decreasing the luminescence properties of the final labeled biospecific binding reactant, other functional groups are suitably protected against conditions and reactants used in solid-phase synthesis and it is easy to deprotect the functional groups during solid-phase synthesis and/or after the product has been released from the solid support.

It is, however, not absolutely necessary that the final biospecific binding reactant is bound to the solid phase already when the labeling reactant is attached to the functional group on the solid phase. The final biospecific binding reactant can be synthesized on the solid phase after the connection of the labeling reactant, or alternatively, the product comprising labeling reactants and optionally also spacer molecules, can be built up on the solid phase and then cleaved therefrom whereafter the cleaved product, before or after having been converted into a lanthanide chelate, is finally reacted in solution with the biospecific binding reactant.

According to one embodiment, a spacer molecule having a transient protecting group is reacted with a functional group on the solid phase and said transient protection group is removed prior to an introduction of the labeling reactant onto the solid phase. As an example of such a spacer molecule can be mentioned 6-aminohexanoic acid having the amino group protected with a transient protecting group, e.g. a group X as mentioned before.

The labeling reactant can be introduced into biomolecules with the aid of peptide synthesizer. The reagent is coupled to an amino tethered solid support or immobilized amino acid by carbodiimide chemistry described in Jones, J., The Chemical Synthesis of Peptides, Oxford Univesity Press, Oxford, 1994, (i.e. the carboxylic acid function of the labeling reagent reacts with the amino group of the solid support or amino acid in the presence of an activator). When the condensation step is completed the transient amino protecting group of the labeling reagent is selectively removed while the material is still attached to the solid support (e.g with piperidine in the case of Fmoc-protecting group). Then second coupling of a labeling reagent or other reagent (amino acid, hapten) is performed as above. When the synthesis of the desired molecule is completed, the material is detached from the solid support and deprotected. Purification can be performed by HPLC techniques. Finally the purified ligand is converted to the corresponding lanthanide(III) chelate by addition of known amount of lanthanide(III) ion, (Mukkala, V.-M. et al. Helv. Chim. Acta 1993, 76, 1361 and M. Kwiatkowski, M. Samiotaki, U. Lamminmäki, V.-M. Mukkala and U. Landegren, Nucleic Acid Res., 1994, Vol 22, 2604–2611).

The invention is further elucidated by the following examples. The structures and the synthetic routes employed in the experimental part are depicted in Schemes 2–4. Scheme 2 illustrates the synthetic procedures for the preparation of the labeling reagent 5. The experimental details are given in Examples 1–4. Scheme 3 illustrates synthetic procedures for the preparation of the labeling reagent 10. The experimental details are given in Examples 5–8. Introduction of the labeling reagent 5 into an oligopeptide structure using machine assisted solid phase chemistry is described in Example 9. A solid phase method for the preparation of an estradiol conjugate tethered to four labeling reagents 5 is illustrated in Scheme 4. In order to increase the coupling efficiency, an aliphatic spacer molecule (6-aminohexanoic acid) is introduced between the labeling reagents. The experimental details are given in Example 10.

EXPERIMENTAL PROCEDURES

Adsorption column chromatography was performed on columns packed with Xieselgel 60 (Merck). Analytical TLC was conducted on silica gel 60 $F_{254}$ plates (Merck) using the following solvent systems. System A: petroleum ether ethyl acetate 5/2 (v/v); System B: $CHCl_3$/MeOH 8/2 (v/v). NMR spectra were recorded on a Jeol LA-400 instrument operating at 399.8 and 105.0 MHz for $^1H$ and $^{13}C$, respectively. TMS was used as an internal reference. Coupling constants are given in hertz. IR spectra were recorded on Perkin Elmer 2400 spectrophotometer.

EXAMPLE 1

The Synthesis of Methyl (4-ethynylphenoxy)acetate (2)

A solution of methyl (4-trimethylsilylethynylphenoxy) acetate (20.00 g, 76 mmol) in dichloromethane (400 mL) was deaerated with argon. Tetrabutylammonium fluoride 24.40 g, 91 mmol) was added, and the mixture was stirred for 30 min at ambient temperature. The solution was washed with 10% aqueous citric acid (200 mL), water (5×400 mL), dried over $Na_2SO_4$ and concentrated. The residue was dissolved in diethyl ether and passed through a column filled with silica gel. Evaporation of diethyl ether yielded the title compound as a solid (12.63 g, 83%) which was chromatographically and spectroscopically identical with material synthesized previously (Takalo, H., Hemmilä, I., Sutela, T. and Latva, M, 1996, Helv. Chim. Acta, 79, 789). $R_f$(A) 0.50.

EXAMPLE 2

The Synthesis of tetra(tert-butyl) 2,2',2,2",2'''-{{4-[4'-(methoxycarbonyl-methoxy)phenylethynyl]pyridine-2,6-diyl}bis(methylenenitrilo)}tetrakis (acetate) (3)

A mixture of tetra(tert-butyl) 2,2',2",2'''-[(4-bromopyridine-2,6-diyl)bis(methylene-nitrilo)]tetrakis (acetate) (1) (2.32 g, 3.4 mmol), bis(triphenylphosphine) palladium(II) chloride (0.050 g, 70 mmol) and CuI (0.027 g, 140 mmol) in dry THF (10 mL) and dry triethylamine (10 mL) was deaerated with argon. Compound 2 (0.79 g, 4.1 mmol) was added and the mixture was stirred for 7 h at 50° C. The cooled solution was filtered, the filtrate evaporated and redissolved in chloroform (150 mL). The solution was washed with water (3×150 mL), dried and evaporated. Purification on silica gel (System A) yielded the title compound as an oil (2.01 g, 75%). $R_f$(A) 0.40. IR (film): 2212 (C≡C), 1750 (C=O), 1730 (C=O). $^1H$ NMR ($CDCl_3$): δ 1.47 (36H, s), 3.50 (8H, s), 3.83 (3H, s), 4.02 (4H, s), 4.67 (2H, s), 6.90 (2H, d, J 9.0), 7.46 (2H, d, J 9.0), 7.60 (2H, s). $^{13}C$ NMR ($CDCl_3$): δ 28.19, 52.36, 55.86, 59.73, 65.18, 81.25, 86.96, 92.89, 114.74, 115.90, 122.66, 132.68, 132.69, 133.44, 158.19, 168.98, 171.11.

EXAMPLE 3

The Synthesis of 4-{2'''-,6'''-bis{N,N-bis[(tert-butoxycarbonyl)methyl]-aminomethyl}-4'''-pyridyl}ethynyl}phenoxymethylacetic acid (4)

Compound 3 (1.98 g, 2.5 mmol) was dissolved in 0.25 M KOH (25 mL, 98% EtOH, 2% water) and the mixture was stirred for 10 min at room temperature. The reaction was quenched by addition of 10% aqueous citric acid (100 mL). The resulting suspension was extracted with chloroform (100 mL). The organic layer was washed with citric acid (2×100 mL) and water (2×100 mL). Evaporation to dryness yielded the title compound as a solid (87%). $R_f$(B) 0.4. IR (film): 2209 (C≡C). $^1H$ NMR (DMSO-$d_6$): δ 1.41 (36H, s), 3.48 (8H, s), 3.89 (4H, s), 4.76 (2H, s), 6.99 (2H, d, J 8.8), 7.52 (2H, d, J 8.8), 7.52 (2H, s).

EXAMPLE 4

The Synthesis of 6-{N-{4-{2"-{2'",6'"-bis{N,N-bis[(tert-butoxycarbonyl)methyl]aminomethyl}-4'''-pyridyl}ethynyl}phenoxymethyl-carbonyl}amino}-2-[-N-(fluorenylmethyloxycarbonyl)amino]hexanoic acid (5)

Compound 4 (0.75 g, 0.98 mmol) and N-hydroxysuccinimide (HO-Su) (0.13 g, 1.1 mmol) were dissolved in dry dioxane (30 mL). DCC (0.23 g, 1.1 mmol) predissolved in dry dioxane (5 mL) was added and the mixture was stirred for 4 h at room temperature and filtered on a solution of α-Fmoc-lysine hydrochloride (0.88 g, 2.2 mmol) in the mixture of dry DMF (15 mL) and pyridine (5 mL). After 4 h, ethanol free chloroform (150 mL) was added and the solution was washed with 10% aq. citric acid (3×50 mL) and water (50 mL), dried (4 Å molecular sieves) and concentrated. Purification on silica gel (System B) yielded the title compound as a solid (56%). IR (film): 3315 (OH), 2210 (C≡C), 1681 (C=O). $^1H$ NMR (DMSO-$d_6$): δ 1.23 (2H, m), 1.40 (36H, s), 3.10 (2H, m), 3.30 (4H, m), 3.42 (8H, s), 3.89 (4H, s), 3.73 (1H, m), 4.24 (5H, m), 4.51 (2H, m), 7.01 (2H, d, J 8.8), 7.32 (2H, t, J 7.2), 7.40 (2H, t, J 7.2), 7.51 (2H, s), 7.52 (2H, d, J 8.8), 7.69 (2H, d, J 7.5), 7.88 (2H, d, J 7.5), 8.17 (1H, t, J 6.3), 8.32 (1H, s).

EXAMPLE 5

The Synthesis of tetra(tert-butyl) 2,2',2",2'''-{{6,6'-[4'-(methoxy-carbonylmethoxy)phenylethynyl]-1H-pyrazol-1",3"-diyl}bis(pyridine)-2,2'diyl}-bis (methylenenitrilo)}tetrakis(acetate) (7)

A mixture of compound 6 (2.14 g, 2.5 mmol), bis (triphenylphosphine)palladium(II) chloride (35 mg, 50 μmol), and CuI (19 mg, 0.1 mmol) in dry DMF (12.5 mL) containing dry triethylamine (10 mL) was deaerated with argon. The mixture was stirred overnight at 35° C. The solution was filtered and concentrated. The residue was dissolved in chloroform (100 mL), washed with water (3×100 mL), dried and concentrated. Purification was performed on silica gel column (System A). Yield was 1.12 g (45%). $R_f$(A) 0.2. IR (film): 1737 (C=O), 1143 (C—O, C=O). $^1H$ NMR (DMSO-$d_6$): δ 1.38 (18H, s), 1.42 (18H, s), 3.49 (4H, s), 3.52 (4H, s), 3.72 (3H, s), 4.00 (2H, s), 4.08 (2H, s), 4.86 (2H, s), 6.98 (2H, d, J 8.9), 7.95 (1H, t, J 7.8), 8.01 (1H, d, J 7.1), 8.88 (1H, s).

EXAMPLE 6

The Synthesis of tetra(tert-butyl) 2,2',2",2'''-{{6,6'-{2-[4'-(methoxy-carbonylmethoxy)phenyl]ethyl}-1H-pyrazole-1",3"-diyl}bis(pyridine)-2,2'diyl}bis (methylenenitrilo)}tetrakis(acetate) (8)

Compound 7 (0.82 g, 0.88 mmol) was dissolved in dry methanol (60 mL). Pd/C (0.16 g; 10%) was added and the reaction was stirred for 4 h under hydrogen atmosphere. The solution was filtered through celite and evaporated. Yield was 0.57 g (70%). $R_f$(A) 0.3. IR(film): 1738 (C=O), 1143 (C—O). $^1H$ NMR (DMSO-$d_6$): δ 1.37 (18H, s), 1.41 (18H, s), 2.88 (2H, d, J 8.4), 3.18 (2H, d, J 8.4), 3.48 (4H, s), 3.49 (4H, s), 3.68 (3H, s), 3.98 (2H, s), 4.04 (2H, s), 4.73 (2H, s), 6.82 (2H, d, J 8.4), 7.18 (2H, d, J 8.4), 7.47 (1H, d, J 7.6), 7.55 (1H, d, J 7.6), 7.87 (1H, d, J 7.8), 7.88 (1H, t, J 7.6), 7.96 (1H, t, J 7.8), 7.98 (1H, t, J 7.6), 8.44 (1H, s).

EXAMPLE 7

The Synthesis of {4'-{2''-{1''',3'''-bis[(tert-butoxycarbonyl)methyl]-aminometh-5''''-yl-2''''-pyridyl}-1H-pyrazol-4'''-yl}ethylphenoxy}acetic acid (9)

The title compound (9) was synthesized as described above for 4 in Example 2 by using compound 8 (0.57 g, 0.62 mmol) as the starting material. Purification was performed on silica gel (petroleum ether/ethyl acetate 5/2→MeOH/CHCl$_3$ 2/8) Yield was 100%. R$_f$(B) 0.95. $^1$H NMR (DMSO-d$_6$): δ 1.37 (18H, s), 1.41 (18H, s), 2.84 (2H, d, J 8.4), 3.15 (2H, d, J 8.4) 3.47 (4H, s), 3.48 (4H, s), 3.98 (2H, s), 4.03 (2H, s) 4.17 (2H, s), 6.74 (2H, d, J 8.4), 7.11 (2H, d, J 8.4), 7.46 (1H, d, J 7.8), 7.55 (1H, d, J 6.9), 7.87 (1H, d, J 7.8), 7.88 (1H, t, J 7.9), 7.95 (1H, d, J 6.9), 7.98 (1H, t, J 7.8), 8.44 (1H, s).

EXAMPLE 8

The Synthesis of 6-{N-{4'-{2''-{1''',3'''-bis[(tert-butoxycarbonyl)-methyl]aminometh-5''''-yl-2''''-pyridyl}-1H-pyrazol-4'''-yl}ethyl}phenoxymethyl-carbonyl}amino-2-[N-(fluorenylmethyloxycarbonyl)amino]hexanoic acid (10)

The title compound (10) was synthesized as described in Example 4 for 5 by using 9 as the starting material. $^1$H NMR (DMSO-d$_6$): δ 1.05 (1H, m), 1.20 (2H, m), 1.36 (18H, s), 1.40 (18H, s), 1.60 (2H, s), 1.71 (2H, m), 2.86 (2H, t, J 7.9), 3.10 (2H, m), 3.18 (2H, m), 3.30 (4H, s), 3.38 (4H, s), 3.80 (1H, m), 3.97 (2H, s), 4.03 (2H, s), 4.23 (4H, m), 4.39 (2H, s), 6.85 (2H, d, J 8.6), 7.17 (2H, d, J 8.6), 7.31 (2H, 7, J 7.4), 7.40 (2H, t, J 7.4), 7.47 (1H, d, J 7.7), 7.55 (1H, d, J 7.7), 7.70 (2H, d, J 7.3), 7.88 (1H, d, J 7.6), 7.99 (1H, d, J 7.8), 8.44 (1H, s).

EXAMPLE 9

Introduction of the Labeling Reagent into Oligopeptides

Figure 1:
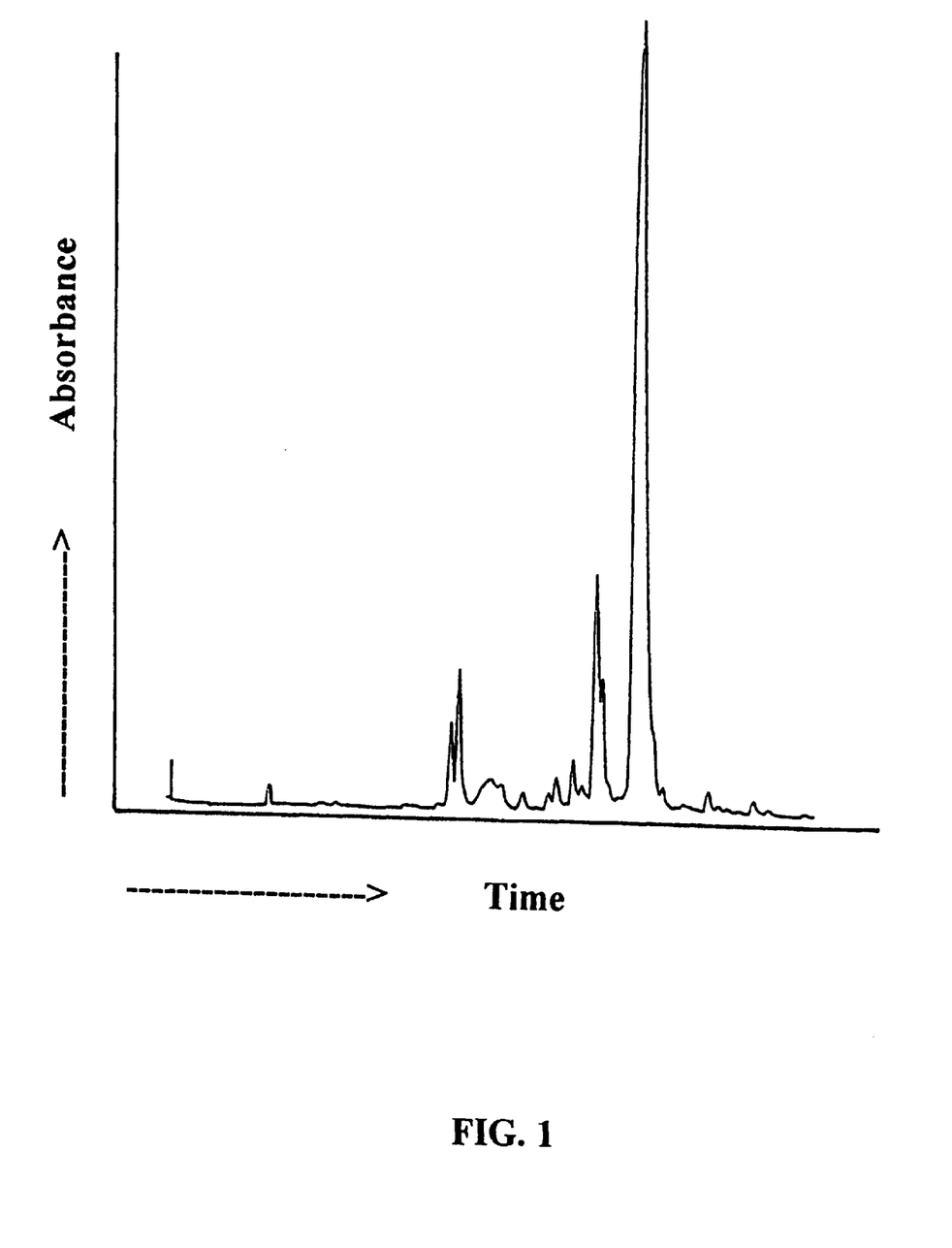
FIG. 1 shows reversed phase HPLC trace of the oligopeptide conjugate R-E-S-Q-N-Y-P-I-V-X$^1$—CONH$_2$ after deprotection (crude reaction mixture). X$^1$ is the deprotected labeling reagent 5 coupled to the COOH terminus of the oligopeptide.
Figure 2:
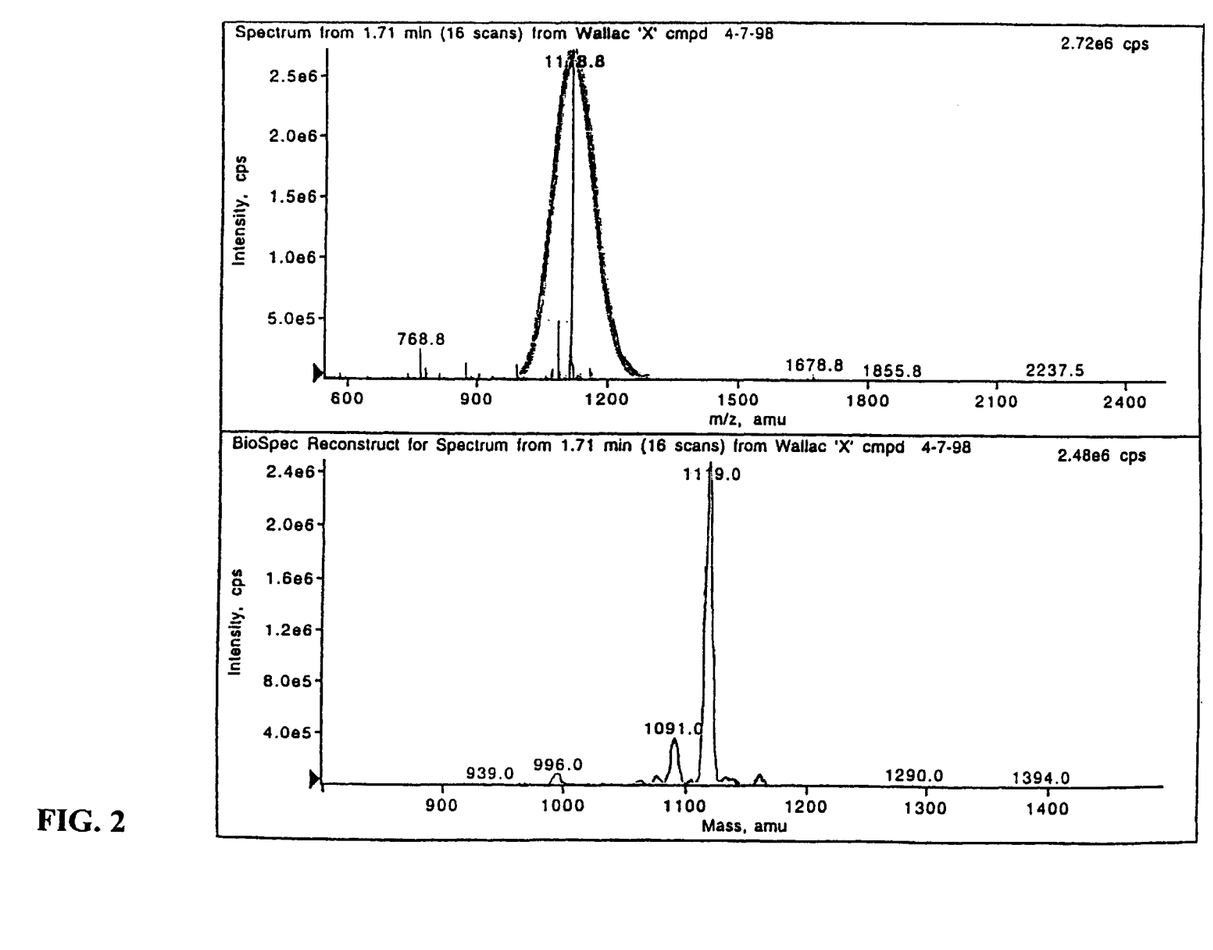
FIG. 2 shows electron spray mass spectrum of the oligopeptide conjugate (major peak of the HPLC profile shown in FIG. 1).

In order to demonstrate the applicability of the ligands prepared to oligopeptide labeling, a sequence R-E-S-Q-N-Y-P-I-V-X$^1$—CONH$_2$ was synthesized on a Perkin Elmer 433A peptide synthesizer (5 μmol scale) using standard Fmoc chemistry. The ligand 5 was introduced in the first coupling step using a prolonged coupling time (1 h instead of 30 min). When the chain assembly was completed, the oligopeptide was deprotected and purified by HPLC. A typical HPLC trace (a crude reaction mixture) is shown in FIG. 1. The product was confirmed by electron-spray mass spectrometry (FIG. 2). Finally the purified material was converted into the corresponding europium(III) chelate using the standard protocol.

EXAMPLE 10

Labeling of Estradiol with Four Europium(III) Chelates

The labeling reagent 5 was introduced into an amino derivatized solid support as described in Example 9. After removal of the α-Fmoc protecting group a Fmoc-aminohexanoic acid was coupled. These cycles were repeated three times and an estradiol derivative tethered to a carboxylic acid linker was introduced as the last coupling step. Deprotection and purification were performed as described in Example 9.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

Scheme 1

5

Scheme 3

-continued

9

1. HO—Su/DCC
2. α-Fmoc-L-Lys

10

What is claimed is:

1. A labeling reactant of formula (I) suitable for labeling of a biospecific binding reactant using solid-phase synthesis (I)

wherein
- -A- is a bivalent aromatic structure capable of absorbing light or energy and transferring the excitation energy to a lanthanide ion after the product made by the said solid-phase synthesis has been released from the used solid support, deprotected and converted to a lanthanide chelate;
- -G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR"— and —NR"—CO—), ester (—COO— and —OOC—), disulfide (—S—S—), diaza (—N═N—) and tertiary amine (—NR"-), wherein R" represents an alkyl containing less than 5 carbon atoms;
- R is a protected amino acid residue —CH(NHX)COOH, where X is a transient protecting group, or its active ester, where said ester is an N-hydroxysuccinimido, p-nitrophenol or pentafluorophenol ester; and
- R' is —COOR'" where R'" is an alkyl of 1 to 4 carbon atoms, phenyl or benzyl, which phenyl or benzyl can be substituted or unsubstituted.

2. The labeling reactant according to claim 1 wherein X is fluorenylmethyloxycarbonyl (Fmoc) or tert-butyloxycarbonyl (Boc).

3. The labeling reactant according to claim 1 wherein R'" is methyl, ethyl or tert-butyl.

4. The labeling reactant according to claim 1 wherein the biospecific binding reactant is selected from the group consisting of an antigen, a hapten, a peptide, a receptor ligand, a drug or PNA oligomer.

5. The labeling reactant according to claim 1 wherein -A- is a bivalent aromatic structure selected from the group consisting of the structures disclosed in Scheme 1.

6. The labeling reactant according to claim 1 selected from the group consisting of 6-{N-{4-{2"-{2'",6'"-bis{N,N-bis[(tert-butoxycarbonyl)methyl]aminomethyl}-4'"-pyridyl}ethynyl}phenoxymethyl-carbonyl}amino}-2-[-N-(fluorenylmethyloxycarbonyl)amino]hexanoic acid (5) and 6-{N-{4'-{2"-{1'",3'"-bis[(tert-butoxycarbonyl)methyl]aminometh-5""-yl-2""-pyridyl}-1H-pyrazol-4'"-yl}ethyl}phenoxymethyl-carbonyl}amino-2-[N-(fluorenylmethyloxycarbonyl)amino]hexanoic acid (10).

7. A method of labeling a biospecific binding reactant in a solid-phase synthesis, said method comprising the steps of
a) reacting a labeling reactant of formula (I)

(I)

wherein
- -A- is a bivalent aromatic structure capable of absorbing light or energy and transferring the excitation energy to a lanthanide ion after the product made by the said solid-phase synthesis has been released from the used solid support, deprotected and converted to a lanthanide chelate;
- -G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR"- and —NR"—CO—), ester (—COO— and —OOC—), disulfide (—S—S—), diaza (—N═N—) and tertiary amine (—NR"-), wherein R" represents an alkyl containing less than 5 carbon atoms;

R is a 4-substituted 6-chloro-1,3,5-triazine-2-amine, isothiocyanato, bromoacetamido, iodoacetamido, pyridyldithio, amino, thiol, carboxylic acid residue or its active ester, a protected amino acid residue —CH(NHX)COOH, where X is a transient protecting group, or its active ester, where said ester is an N-hydroxysuccinimido, p-nitrophenol or pentafluorophenol ester; and R' is —COOR''' where R''' is an alkyl of 1 to 4 carbon atoms, phenyl or benzyl, which phenyl or benzyl can be substituted or unsubstituted, with a functional group which is bound to a solid phase, b) cleaving the product obtained in step a) from the solid phase, converting R' to —COOH, and removing optional protection groups, c) converting the product from step b) to a lanthanide chelate, and d) in case the functional group mentioned in step a) is not part of the final biospecific binding specific reactant, attaching said biospecific binding reactant to the lanthanide chelate obtained in step c).

8. The method according to claim 7 wherein X in the labeling reactant is fluorenylmethyloxycarbonyl (Fmoc) or tert-butyloxycarbonyl (Boc).

9. The method according to claim 7 wherein R''' in the labeling reactant is methyl, ethyl or tert-butyl.

10. The method according to claim 7 wherein the biospecific binding reactant is selected from the group consisting of an antigen, a hapten, a peptide, a receptor ligand, a drug or PNA oligomer.

11. The method according to claim 7 wherein -A- in the labeling reactant is a bivalent aromatic structure selected from the group consisting of the structures disclosed in Scheme 1.

12. The method according to claim 7 wherein the labeling reactant is selected from the group consisting of 6-{N-{4-{2''-{2''',6'''-bis{N,N-bis[(tert-butoxycarbonyl)methyl]aminomethyl}-4'''-pyridyl}ethynyl}phenoxymethylcarbonyl}amino}-2-[N-(fluorenylmethyloxycarbonyl)amino]hexanoic acid (5) and 6-{N-{4'-{2''-{1''',3'''-bis[(tert-butoxycarbonyl)-methyl]aminometh-5''''-yl-2''''-pyridyl}-1H-pyrazol-4'''-yl}ethyl}phenoxymethyl-carbonyl}amino-2-[N-(fluorenylmethyloxycarbonyl)amino]hexanoic acid (10).

13. A method of labeling a biospecific binding reactant with an exact, predetermined number of labeling reactants of formula (I) in a solid-phase synthesis, said method comprising the steps of a) reacting a labeling reactant of formula (I)

(I)

wherein

-A- is a bivalent aromatic structure capable of absorbing light or energy and transferring the excitation energy to a lanthanide ion after the product made by the said solid-phase synthesis has been released from the used solid support, deprotected and converted to a lanthanide chelate;

-G- is a bridge replacing a hydrogen atom in A and is formed of one to ten moieties, each moiety being selected from the group consisting of phenylene, alkylene containing 1–12 carbon atoms, ethynediyl (—C≡C—), ether (—O—), thioether (—S—), amide (—CO—NH— and —NH—CO— and —CO—NR''- and —NR''—CO—), ester (—COO— and —OOC—), disulfide (—S—S—), diaza (—N—N—) and tertiary amine (—NR''-), wherein R'' represents an alkyl containing less than 5 carbon atoms;

R is a protected amino acid residue —CH(NHX)COOH, where X is a transient protecting group, or its active ester, where said ester is an N-hydroxysuccinimido, p-nitrophenol or pentafluorophenol ester; and R' is —COOR''' where R''' is an alkyl of 1 to 4 carbon atoms, phenyl or benzyl, which phenyl or benzyl can be substituted or unsubstituted, with a functional group which is bound to a solid phase, b) removing the transient protecting group X and optionally other transient protecting groups attached to the solid phase, c) reacting the labeling reactant of formula (I) to a deprotected functional group attached to the solid phase, d) optionally repeating the steps b) to c) the number of times necessary to achieve the exact, predetermined number of labeling reactants of formula (I) bound to the solid phase, e) cleaving the product obtained after the final step c) from the solid phase, converting R' to —COOH, removing the group or groups that have bound the product to the solid phase, and removing optional protecting groups, and f) converting the product from step e) to a lanthanide chelate.

14. The method according to claim 13 wherein step f) is followed by reacting the biospecific binding reactant with the lanthanide chelate obtained in step f), to obtain the labeled biospecific binding reactant.

15. The method according to claim 13 wherein the biospecific binding reactant is reacted with the product containing the labeling reactants while said product still is bound to the solid phase.

16. The method according to claim 13 wherein the biospecific binding reactant is built up in the solid phase synthesis.

17. The method according to claim 13 wherein a spacer molecule having a transient protecting group is reacted with a functional group on the solid phase and said transient protection group is removed prior to an introduction of the labeling reactant onto the solid phase.

18. The method according to claim 13 wherein X in the labeling reactant is fluorenylmethyloxycarbonyl (Fmoc) or tert-butyloxycarbonyl (Boc).

19. The method according to claim 13 wherein R''' in the labeling reactant is methyl, ethyl or tert-butyl.

20. The method according to claim 13 wherein the biospecific binding reactant is selected from the group consisting of an antigen, a hapten, a peptide, a receptor ligand, a drug or PNA oligomer.

21. The method according to claim 13 wherein -A- in the labeling reactant is a bivalent aromatic structure selected from the group consisting of the structures disclosed in Scheme 1.

22. The method according to claim 13 wherein the labeling reactant is selected from the group consisting of 6-{N-{4-{2"-{2'",6'"-bis{N,N-bis[(tert-butoxycarbonyl)methyl]aminomethyl}-4'"-pyridyl}ethynyl}phenoxymethylcarbonyl}amino}-2-[-N-(fluorenylmethyloxycarbonyl)amino]hexanoic acid (5) and 6-{N-{4'-{2"-{1'",3'"-bis[(tert-butoxycarbonyl)-methyl]aminometh-5""-yl-2""-pyridyl}-1H-pyrazol-4'"-yl}ethyl}phenoxymethylcarbonyl}amino-2-[N-(fluorenylmethyloxycarbonyl)amino]hexanoic acid (10).

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      oligopeptide conjugate
<220> FEATURE:
<223> OTHER INFORMATION: this peptide has a deprotected labeling reagent
      coupled to its COOH terminus

<400> SEQUENCE: 1

Arg Glu Ser Gln Asn Tyr Pro Ile Val
 1               5